United States Patent [19]
Xue et al.

[11] Patent Number: 5,840,038
[45] Date of Patent: Nov. 24, 1998

[54] METHOD AND APPARATUS FOR SIGNAL AVERAGING AND ANALYZING HIGH RESOLUTION P WAVE SIGNALS FROM AN ELECTROCARDIOGRAM

[75] Inventors: Qiuzhen Xue, Germantown; Shankara Reddy, Cedarburg, both of Wis.

[73] Assignee: Marquette Medical Systems, Inc., Milwaukee, Wis.

[21] Appl. No.: 865,155

[22] Filed: May 29, 1997

[51] Int. Cl.$^6$ .................................................. A61B 5/0452
[52] U.S. Cl. ......................................................... 600/512
[58] Field of Search ................................... 600/508, 509, 600/510, 512, 515, 516, 517, 521

[56] References Cited

U.S. PATENT DOCUMENTS

| | | | |
|---|---|---|---|
| 4,422,459 | 12/1983 | Simson | 128/702 |
| 4,458,692 | 7/1984 | Simson | 128/705 |
| 4,565,201 | 1/1986 | Lass | 128/696 |
| 4,883,065 | 11/1989 | Kelen | 128/711 |
| 5,046,504 | 9/1991 | Albert et al. | 128/696 |
| 5,205,295 | 4/1993 | Del Mar et al. | 128/711 |
| 5,341,811 | 8/1994 | Cano | 128/696 |

OTHER PUBLICATIONS

Rhyne VT, "A Comparison of Coherent Averaging Techniques for Repetitive Biological Signals", Medical Research Engineering, 22–26, 1969.

Berbari EJ, Lazzara R, Samet P, Scherlag BJ, "Noninvasive techniques for detection of electrical activity during P-R segment", Circulation 48:1005, 1973.

Vincent R, English MJ, Mackintosh AF, Stroud N, Chamberlain DA, Woollons DJ, "A flexible signal–averaging system for cardiac waveforms", Journal of Biomedical Engineering, 2:15–24, 1980.

Simson MB, "Use of Signals in the Terminal QRS Complex to Identify Patients with Ventricular Tachycardia After Myocardial Infarction", Circulation, 64:234, 1981.

Abboud S, Belhassen B, Laniado S, Sadeh D, "Non–Invasive Recording of Late Ventricular Activity Using an Advanced Method in Patients with a Damaged Mass of Ventricular Tissue", Journal Electrocardiology, 16:245–252, 1983.

Koeleman ASM, van der Akker TJ, Ros HH, Janssen RJ, Rompelman O, "Estimation of accuracy of P wave and QRS complex occurrence times in the ECG: The accuracy for simplified theoretical and computer simulated waveforms", Signal Processing 7: 389–405, 1984.

Craelius W, Restivo M, Assadi MA, El–sherif N, "Criteria for Optimal Averaging of Cardiac Signals", IEEE Transactions of Biomedical Engineering, BME–33:957–966, 1986.

Reddy BRS, Christenson DW, and Rowlandson GI, "High resolution ECG on a standard ECG cart", Journal of Electrocardiology, 21: S74–S79, 1988.

Scott WA, Donnerstien RL, "Alignment of P waves for signal averaging", PACE 13:1559–1562, 1990.

(List continued on next page.)

*Primary Examiner*—Scott M. Getzow
*Attorney, Agent, or Firm*—Michael Best & Friedrich LLP

[57] ABSTRACT

A method and apparatus for signal averaging and analyzing high resolution P wave signals from an electrocardiogram. The method and apparatus for averaging the P wave portion of ECG signals includes sensing human ECG signals having at least a QRS portion and a P wave portion, detecting the QRS portion of the ECG signals, suppressing the QRS portion of the ECG signals, generating a P wave detection function from the wave portion of the ECG signals, cross correlating the P wave portions of the ECG signals and averaging the cross correlated P wave signals. The method and apparatus for analyzing high resolution P wave signals includes averaging at least a portion of the ECG signals, filtering the averaged signals, deriving the vector magnitude (VM) of the filtered averaged signals, determining the base noise level, and setting the P onset and P offset of the VM signals above the noise level.

29 Claims, 19 Drawing Sheets

OTHER PUBLICATIONS

Fukunami M. et al. "Detection of patients at risk for paroxysmal atrial fibrillation during sinus rhythm by P wave triggered signal–averaged electrocardiogram", Circulation. 83:162–169, 1991.

Guidera SA, Steinberg JS. "The signal–averaged P wave duration: a rapid and non–invasive marker of atrial fibrillation", Journal of American College of Cardiology 21:1645–1651, 1993.

Chauvin M, Cillard J–P, Koenig A, Brechenmaker C. "P–wave signal–averaged ECG: New algorithms for detecting patients at risk of atrial fibrillation", (Abstract), Circulation, 90: I–437, 1994.

Stafford PJ, Robinson D, Vincent R. "Optimal analysis of the signal–averaged P wave in patients with paroxysmal atrial fibrillation", British Heart Journal, 74:413–418, 1995.

Stafford PJ, Turner I, Vincent R. "Quantitative analysis of signal–averaged P waves in idiopathic paroxysmal atrial fibrillation", American Journal Cardiol. 68:751–755, 1991.

Steinberg JS. "Value of P wave signal–averaged ECG for predicting atrial fibrillation after cardiac surgery", Circulation 88:2618–2622, 1993.

METHOD AND APPARATUS FOR SIGNAL AVERAGING AND ANALYZING HIGH RESOLUTION P WAVE SIGNALS FROM AN ELECTROCARDIOGRAM

BACKGROUND OF THE INVENTION

This invention relates to analyzing electrocardiograms and more particularly to a method and apparatus for averaging and analyzing high resolution P wave signals from a surface electrocardiogram.

Atrial fibrillation is a common post operative arrhythmia after coronary artery by-pass surgery and is a re-entrant rhythm. Many physiological factors play a role in the development of atrial fibrillation, but, slow conduction is probably a critical prerequisite in many patients. While atrial fibrillation rarely causes serious or life-threatening complications, it can cause hemodynamic instability in patients with incomplete revascularization, embolic phenomenon and increased length of hospital stay. Therefore, it is desirable to provide a method and apparatus which can identify patients at risk for post-operative atrial fibrillation.

Signal averaging for high-resolution P waves (P-HIRES) signals provides a useful non-invasive tool for evaluation of risk for atrial arrhythmias, particularly atrial fibrillation. To detect P-HIRES, it is necessary to find an accurate alignment of P waves. Since the amplitudes of the P waves are much smaller than the QRS portion of the electrocardiogram, noise removal and more accurate correlation is required for P-HIRES than for QRS signal averaging. Previous P-HIRES studies used the QRS complex as a trigger point as discussed in Engel T R, et el., *Signal Averaged Electrocardiogram in Patients With Atrial Fibrillation or Flutter,* American Heart Journal, 115:592–597, 1988. However, using the QRS complex for triggering P-HIRES might cause some misalignment, mainly due to variations of the P-R intervals from beat-to-beat. The amplitude of the P wave is only about one tenth that of the QRS complex, as is the signal-to-noise ratio. As a result, the task of obtaining a trigger point on the P wave is more difficult than the analysis of high resolution QRS signals.

SUMMARY OF THE INVENTION

In general terms, the invention comprises the method and apparatus of averaging the P wave portion of ECG signals includes sensing human ECG signals having at least a QRS portion and a P wave portion, detecting the QRS portion of the ECG signals, suppressing the QRS portion of the ECG signals, generating a P wave detection function from the P wave portion of the ECG signals, cross correlating the P wave portions of the ECG signals, and averaging the cross correlated P wave signals.

According to another aspect, the invention includes the method and apparatus for determining the onset and offset of the P wave portion of ECG signals and including averaging at least a portion of the ECG signals, filtering the average signals, deriving the vector magnitude of the filtered average signals, determining a baseline noise level, and setting the P onset and P offset of the vector magnitude signals above the noise level.

It is an object of the invention to provide a new and improved method and apparatus for identifying patients at risk of atrial fibrillation.

Another object of the invention is to provide a method and apparatus for P wave averaging for detecting patients at risk for atrial fibrillation.

A further object of the invention is to provide a method and apparatus for signal averaging high resolution P waves.

These and other objects and advantages of the present invention will become more apparent from the detailed description thereof taken with the accompanying drawings.

DETAILED DESCRIPTION OF THE PREFERRED EMBODIMENT

Figure 1:
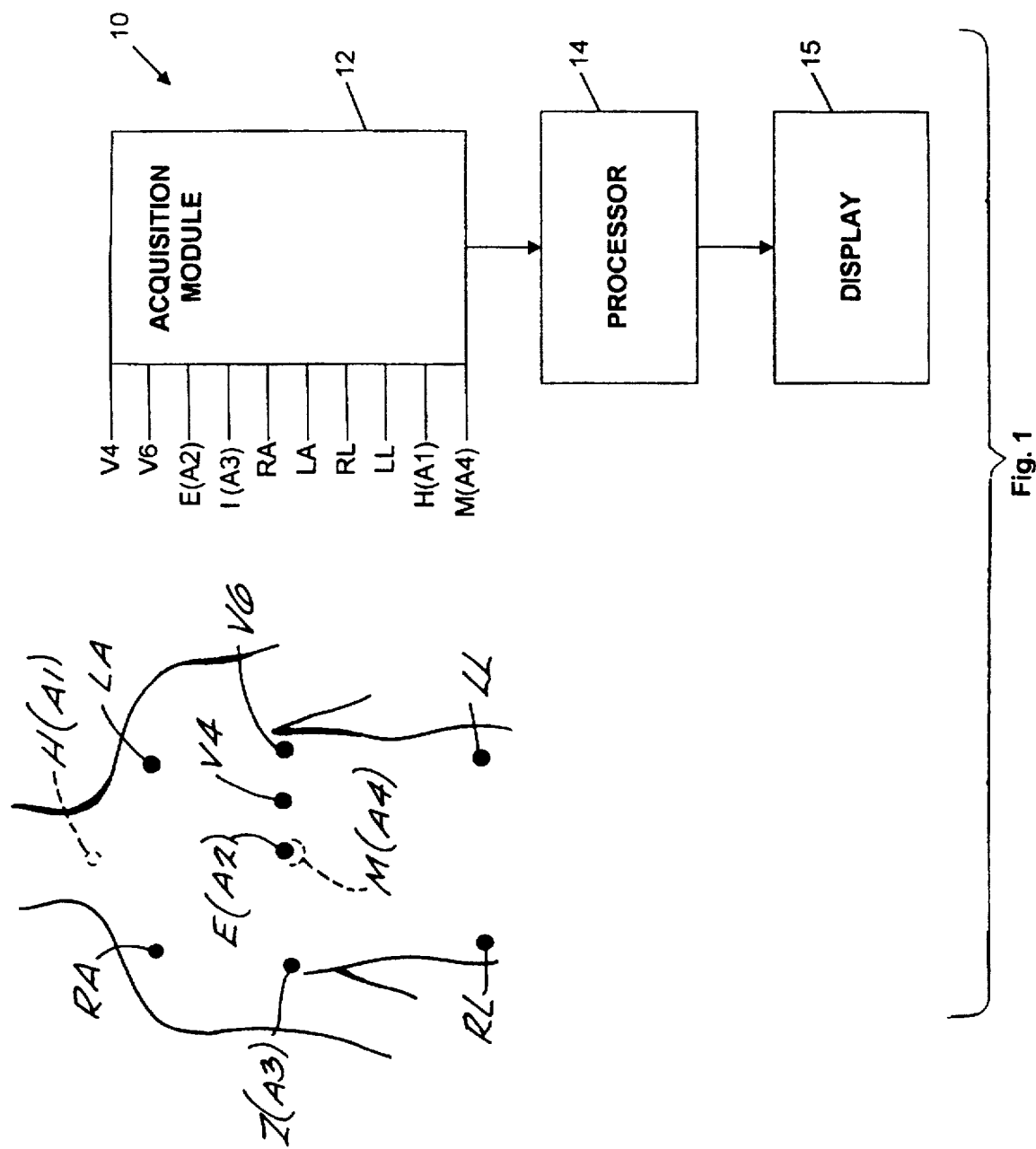
FIG. 1 schematically illustrates a cardiac monitor according to the invention.

FIG. 1 schematically illustrates a cardiac monitor and P wave signal averaging system according to the invention. The system includes an electrocardiogram (ECG) data acquisition module 12 which is connected by lead wires to ten electrodes positioned on the patient's body for sensing high-resolution P wave (P-HIRES) signals from the surface ECG. In particular, the electrodes include: a right arm electrode RA; a left arm electrode LA; chest electrodes V4 at the mid-clavicular line in the fifth intercostal space; V6 at the left mid-auxiliary line in the same horizontal level as V4; E(A2) at the mid-sternum on the same horizontal level as V4 and V6; I(A3) at the mid axillary line on the same horizontal level as V4 and V6; H(A1) at the back of the neck; and M(A4) at the center of the spine of the same horizontal level as V4 and V6. This provides the X lead measurement between electrodes I(A3) and V6; the Y lead measurement between electrodes H(A1) and LL; and the Z lead measurement between electrodes E(A2) and M(A4).

The acquisition module 12 is conventional and includes common mode rejection and filters for removing patient breathing and muscle artifacts. The acquisition module 12 converts the analog lead signals to digital signals and generates conventional ECG leads including the X, Y and Z leads. The combination of electrodes used for determining or deriving the ECG lead signals are well known in the art and will not be discussed here for the sake of brevity.

Figure 2:
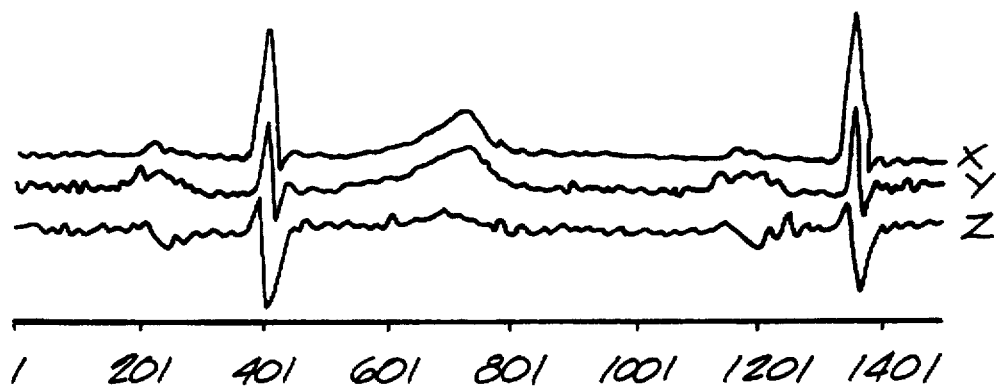
FIG. 2 shows ECG lead signals taken along X, Y and Z axes.

The lead signals are amplified, sampled by the acquisition module at the rate of 1,000 Hz and digitized. The raw X, Y and Z P-HIRES signals are shown in FIG. 2.

The digitized ECG lead signals from the acquisition module 12 are provided to a processor 14 for QRS and P wave signal averaging. QRS signal averaging methods and apparatus are well known in the art and will not be further discussed herein. A display 15 of a type known in the art is connected to the processor 14 for displaying the QRS and P wave signals.

Figure 3:
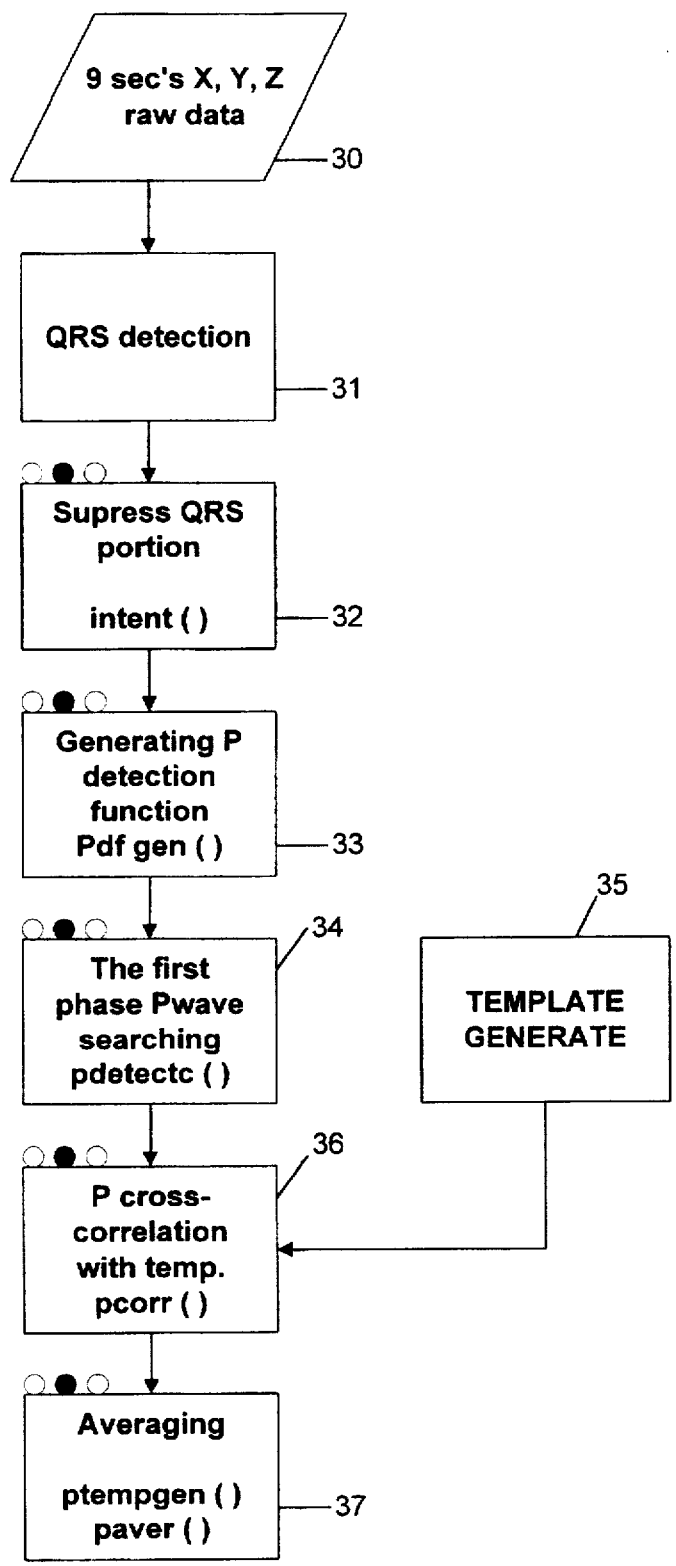
FIG. 3 is a flow diagram showing the P wave averaging method according to the invention.
Figure 11A:
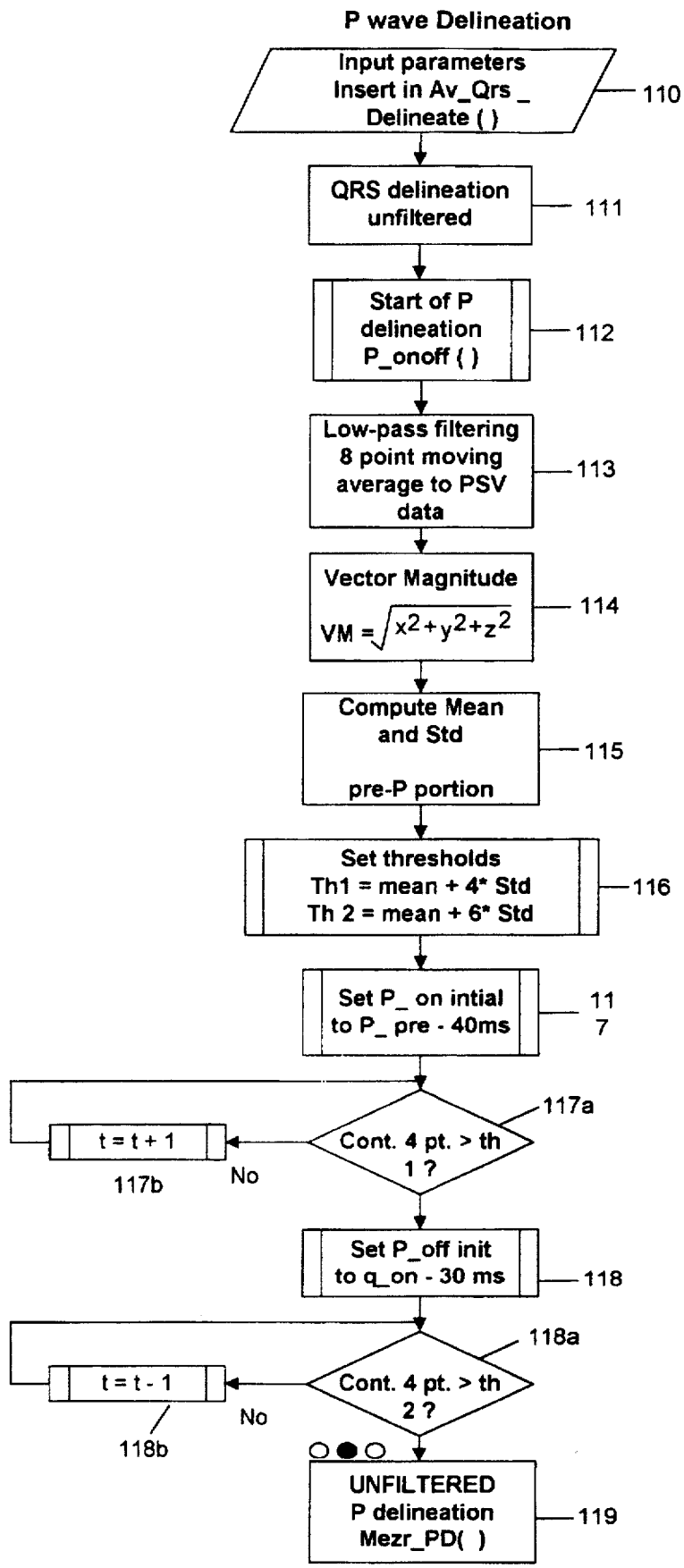
FIGS. 11a and 11b illustrates the unfiltered P wave delineation.
Figure 11B:
Figure 12A:
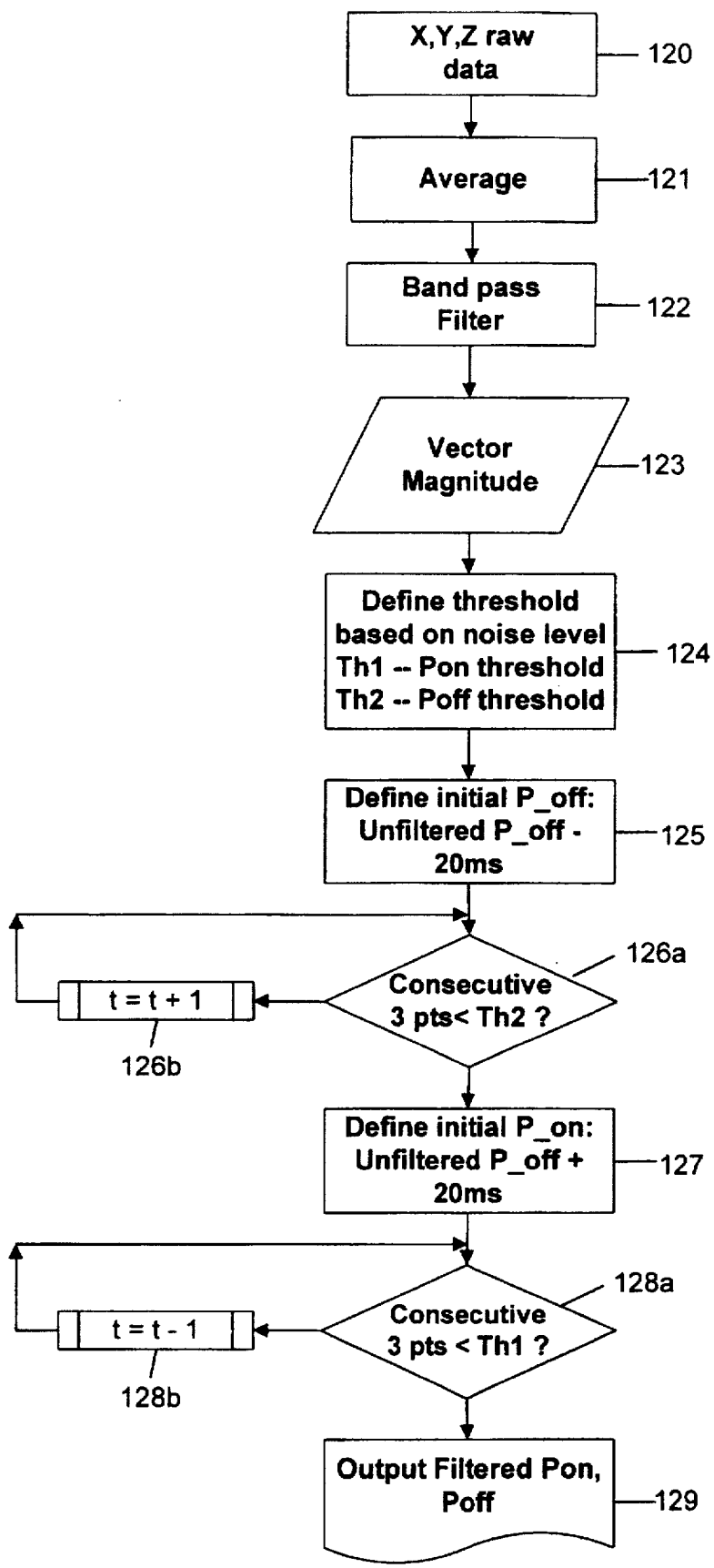
FIGS. 12a and 12b illustrate the filtered P delineation.
Figure 12B:
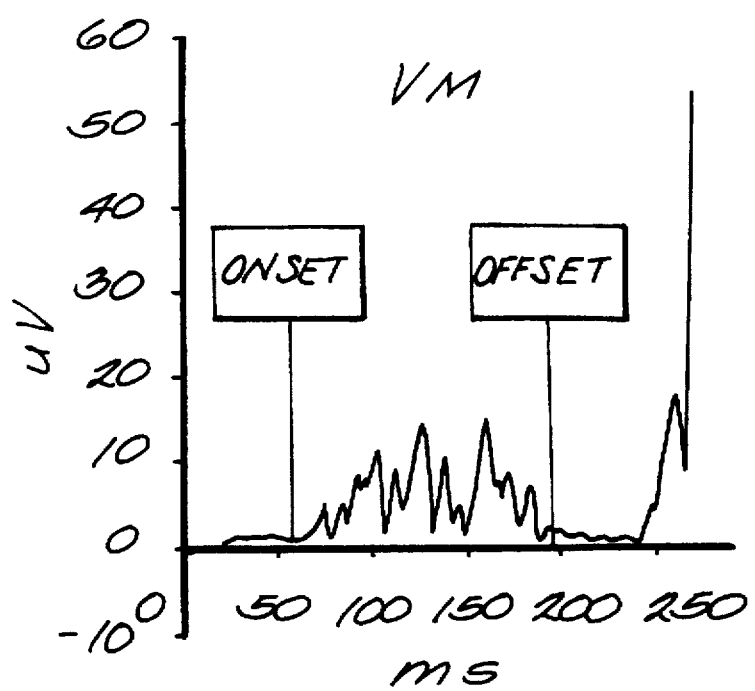

The processor 14 is programmed to perform the methods according to the invention as shown in FIGS. 3, 11 and 12. In particular, the X, Y and Z raw lead signals data are input at 30. The program then performs QRS detection at step 31, QRS suppression at step 32, the generation of the P-detection function at step 33, the first phase P wave searching at step 34, P wave template generation at step 35, P wave cross correlation with the template at step 36, and P wave averaging at step 37.

Figure 4A:
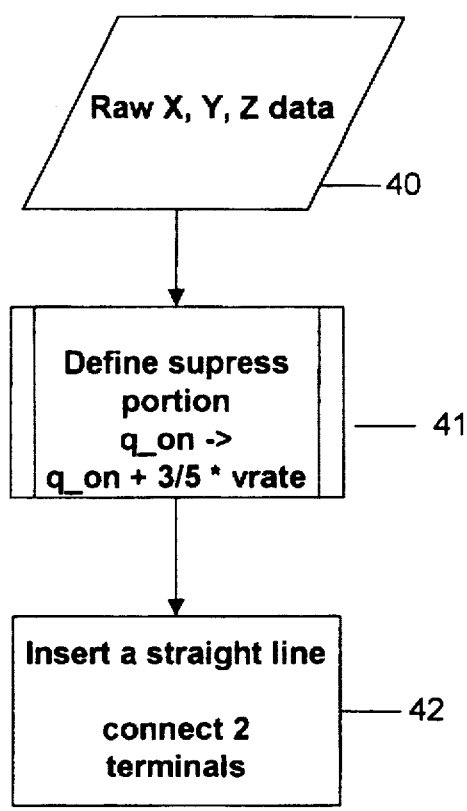
FIGS. 4a and 4b illustrate the QRS suppression portion of the method illustrated in FIG. 3.
Figure 4B:
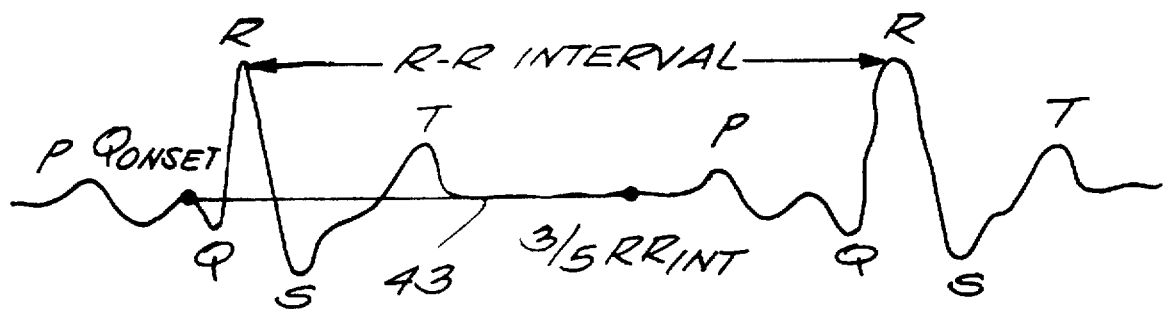
Figure 5A:
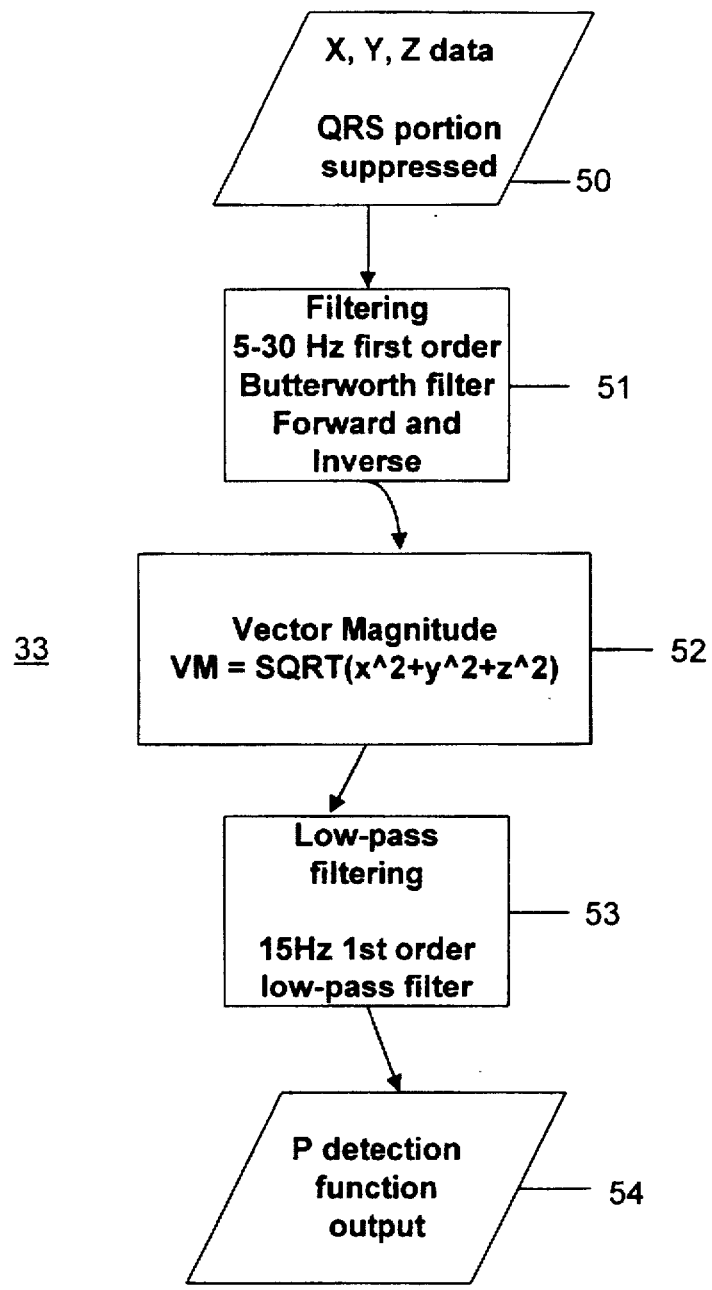
FIG. 5a is a flow diagram showing the P detection function generation portion of the method illustrated in FIG. 3.
Figure 5B:
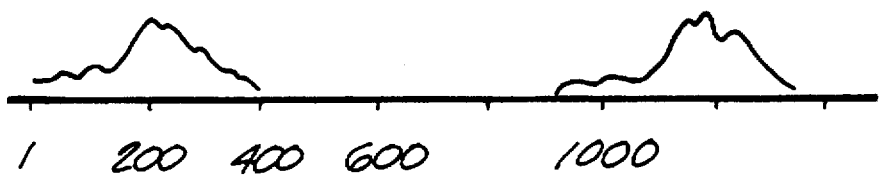
FIG. 5b illustrates the P wave detection function of the vector magnitude signal.

As shown in FIG. 4, the QRS suppression step involves subtracting or suppressing the QRS-T portion of the ECG wave form so that the signal contains the P wave portion only. The P detection function is formed by applying zero-phase-shift band pass filtering, difference and absolute value computation to the data of the X, Y and Z leads as shown in FIG. 5a. The P wave is greatly enhanced in this detection function as shown in FIG. 5b. The P wave searching step 34 involves searching for the P wave in a window ranging from the previous T wave offset to the current QRS onset points. Qualified P waves, i.e., those having an acceptable duration, are cross correlated with a template. Only those P waves whose correlation coefficient with the template is larger than an adjustable pre-selected threshold are averaged. In the preferred embodiment, the threshold is 0.95. Typically, P waves that fail to correlate with the template P wave are beats of ectopic origin and P waves with excessive noise. The averaging process continues until either the target number of beats, e.g., 250, or a desired noise level, e.g., 0.3 pV, is reached. The averaged P wave signals are filtered by a spectral band pass filter used in the standard QRS averaging program of Marquette Medical Systems, Inc. With a band width of 40–250 Hz, and then combined into a vector magnitude (VM). The P wave delineation is first performed in the VM signal of the unfiltered P wave as shown in FIG. 11a, and on the filtered P wave as shown in FIG. 12. Thresholds to detect filtered P onset and P offset points are based on base noise level. The filtered P onset and offset points can be adjusted by the user.

The detection of the QRS signals in step 31 is performed in the conventional manner. A window of data is sampled, which in the preferred embodiment is nine seconds at a sample rate of 1000 Hz with 1 pV resolution. The QRS suppression function in step 32 is shown in FIGS. 4a and 4b. The input signals at 40 comprise the raw X, Y and Z data from the acquisition module 12. First, a suppressed portion is defined in step 41 as a first point which is the Q-wave onset and a second point which is ⅗ of the R—R interval is shown in FIG. 4b. In step 42, a straight line 43 is generated which connects the first and second points. The suppression of this portion of the QRS wave results in the subtraction of the QRS-T portion of the wave form. The remaining portion of the wave form includes the P wave.

The P Detection function generating subroutine 33 is shown in FIG. 5. The input at 50 includes the raw X, Y and Z lead data from the acquisition module 12 and the QRS suppression portion of the wave form from step 42. In step 51, this data is filtered in a 5–30 Hz first order Butterworth filter in the forward and reverse directions. They are then combined into vector magnitude (VM) in step 52 using the expression:

$$VM = \sqrt{X^2 + Y^2 + Z^2}$$

Accordingly, the VM signal is filtered by a first order fifteen Hz low pass filter in step 53. The result is the P filtered detection function in step 54, as shown in FIG. 5b.

Figure 6A:
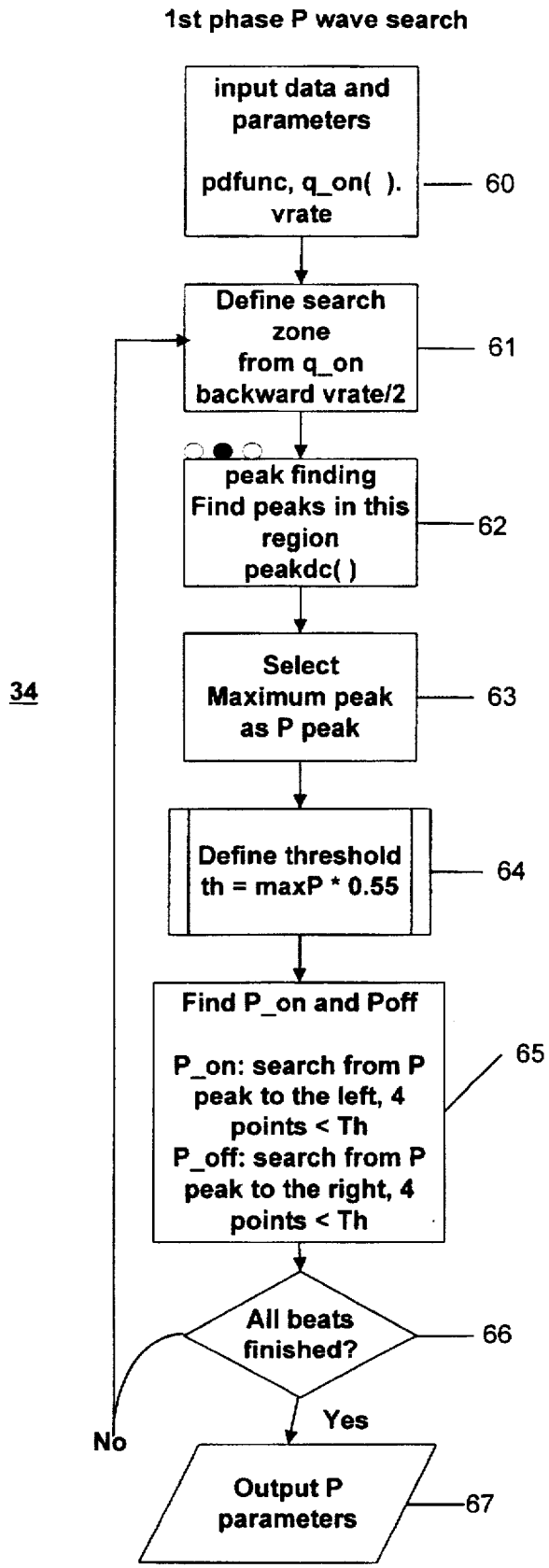
FIGS. 6a, 6b and 6c illustrate the first phase P wave search portion of the method illustrated in FIG. 3.
Figure 6B:
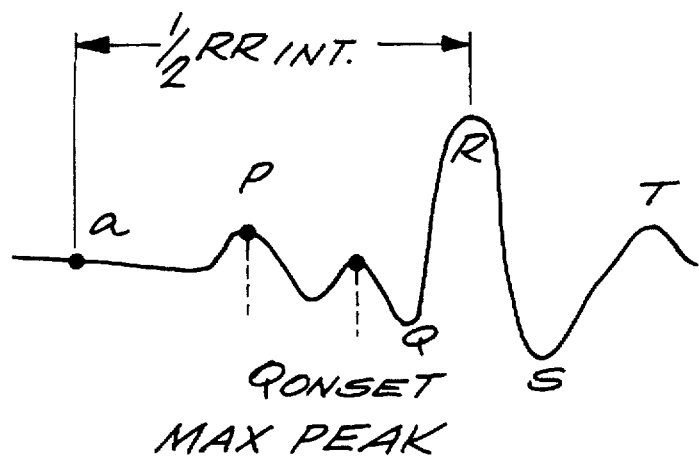
Figure 6C:
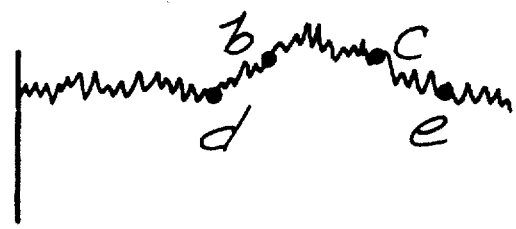

The P wave search 34 involves the location of the P wave onset and offset points as shown in FIG. 6a. The input signals at step 60 include the P detection function from step 54, the Q onset signal from step 41 and the heart rate from the acquisition module 12. In step 61, the search zone is defined from this data. In particular, the program searches backward from the Q onset point to a point which is one-half the R-R interval as shown in FIG. 6b since the P wave lies in this portion of the wave form. The P wave is shown in FIG. 6c to be oscillatory. Therefore, in order to define the P wave, it is first necessary to find all the peaks in the search area at step 62. The maximum peak in the search area may then be selected at step 63 as the P wave peak.

Having located the P wave peak, the program then locates the P wave onset and the P wave offset. Toward this end, the program at step 64 first locates points b and c, which are equal to 0.55 of the maximum peak as shown in FIG. 6c. At step 65, the program then searches four sample points back from point b to locate point d which is P onset and forward four sample points from point c to point e which is P offset. Step 66 determines if the location of P onset and offset has been completed for all beats being measured, which in the illustrated embodiment is nine beats. If complete, the P output parameters are provided at step 67. If not, the program returns to step 61 and repeats the process until it has been completed for all beats.

Figure 7A:
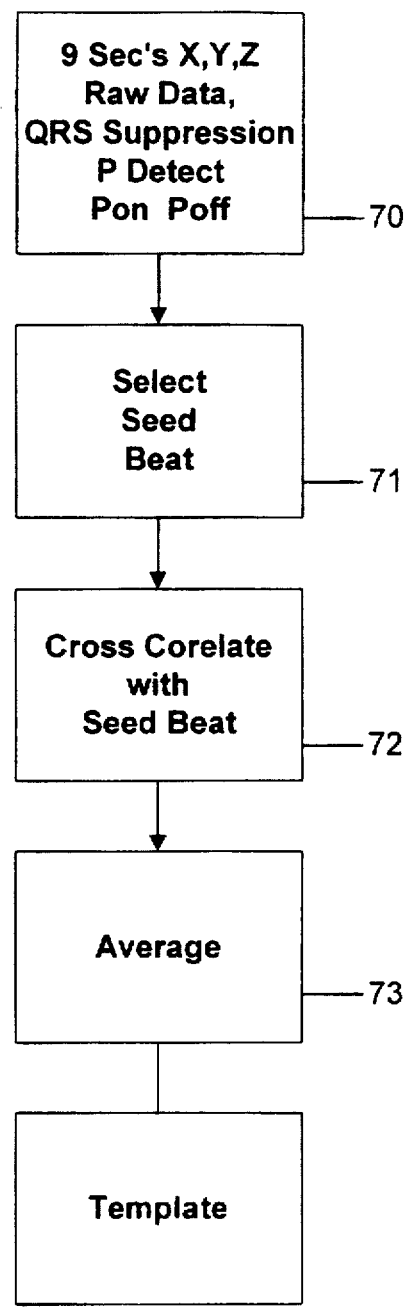
FIGS. 7a and 7b illustrate the template generating portion of the method illustrated in FIG. 3.
Figure 7B:
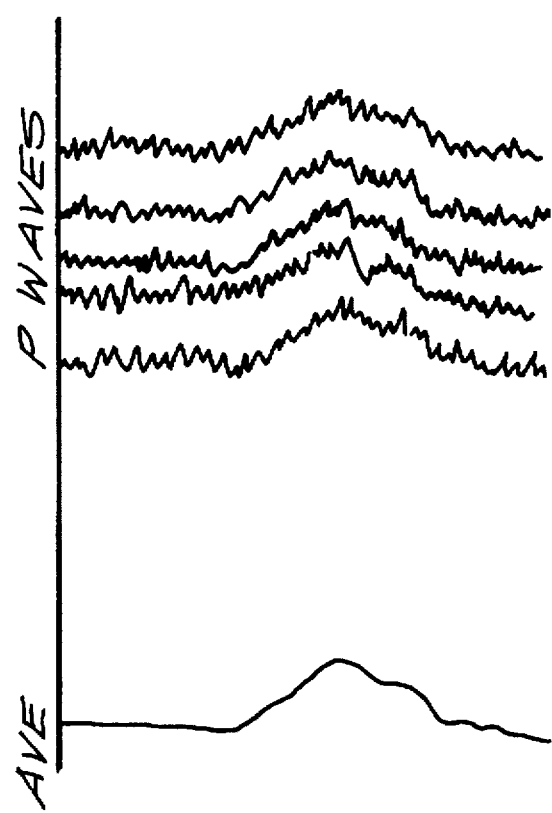

The template generating subroutine 35 is shown in FIG. 7. The input data consists of nine seconds of X, Y and Z axes ECG data, the QRS suppression signal from step 42, the P detect function from step 54 and the Pon and Poff signals from step 67. Next, a seed beat is selected at step 71 based on its matching score with all other beats in the nine second window. The data in the window is displayed on the screen of display 15 of FIG. 1. The user can select a different seed beat if desired. The P Waves from the X, Y and Z signals are cross-correlated with the seed beat in a manner similar to that discussed in connection with FIGS. 8a and 8c below. All P waves which meet the criteria of matching are averaged to form the template in a manner similar to that discussed with respect to FIG. 10. The P waves and the average are shown in FIG. 7b.

Figure 8:
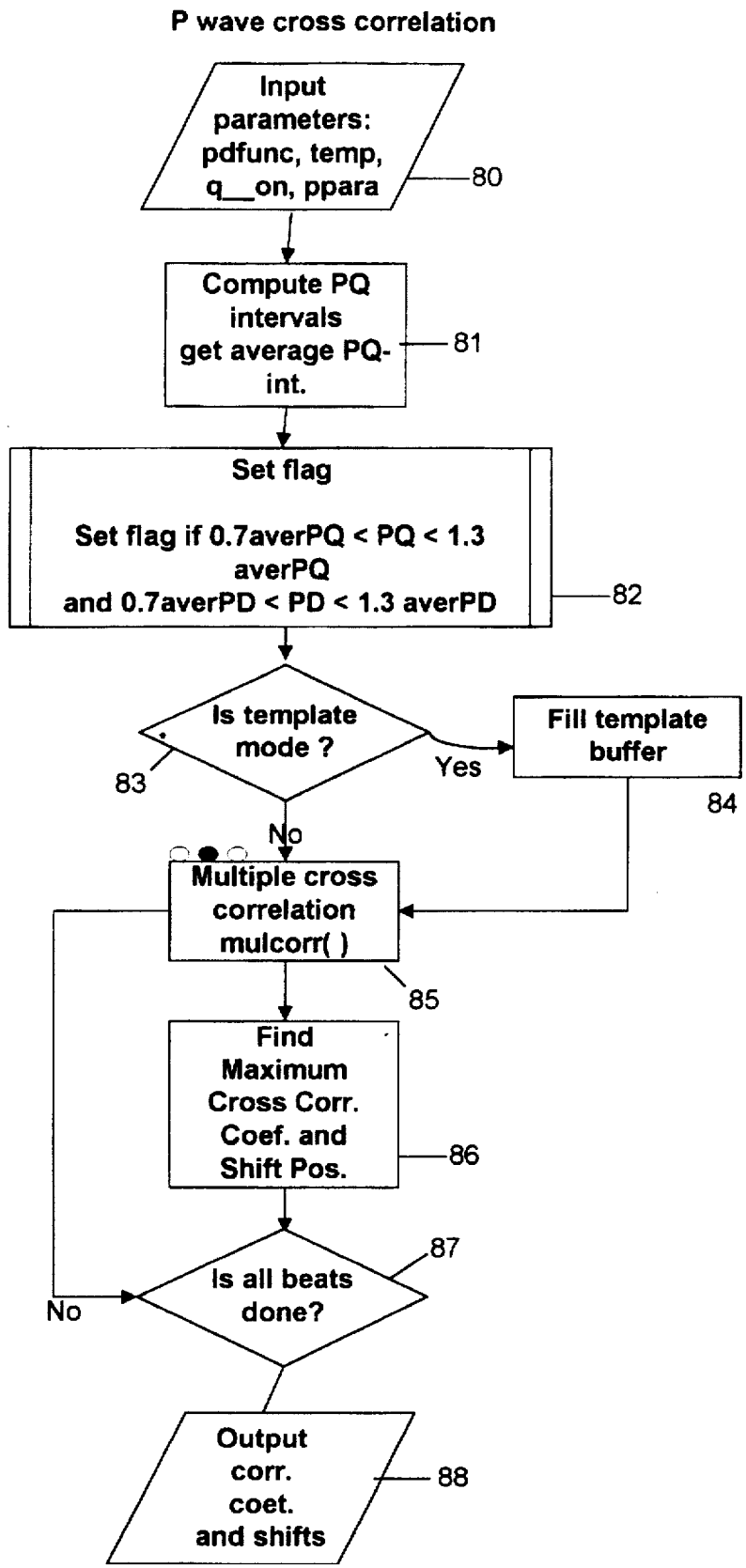
FIGS. 8, 9a and 9b illustrate the P wave cross correlation portion of the method illustrated in FIG. 3.
Figure 9A:
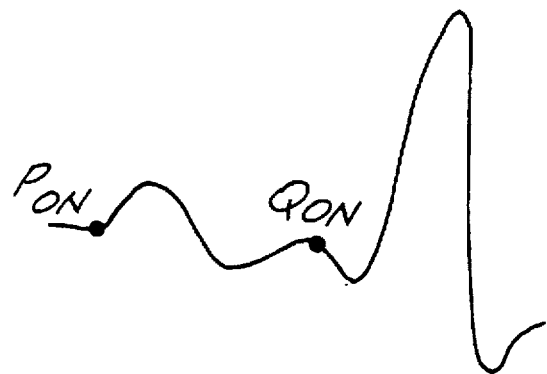
Figure 9B:
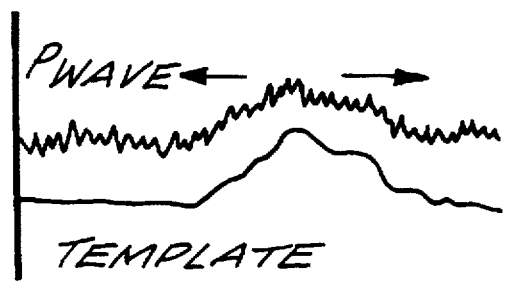

The subroutine for the P wave cross correlation is shown in FIG. 8. The input parameters at 80 are the P detection function from step 54, the template from step 74, the Q wave onset from step 41 and the P wave parameters from step 67. The first step at 81 is to obtain an average of the P-Q interval of the nine seconds of data. This is the time between the P onset from step 65 and the Q onset from step 41 as shown in FIG. 9a. At step 82, a flag is set for all signals in which the P-Q interval is greater than 0.7 and less than 1.3 that of the P-Q average and for all signals in which the P duration is greater than 0.7 and less than 1.3 of the average P duration obtained at step 54. At step 83, the program determines if the system is in the template mode. If so, the template buffer is filled at step 84. Next, at step 85, the multiple cross correlation of the P waves is performed. This involves shifting the P wave to match the template as shown in FIG. 9b. Those P waves which have a 95% correlation with the template and the shift position are selected at step 86. If all of the beats have been correlated, the output correlation coefficient is provided at step 88. If not, steps 85 and 86 are repeated until all beats have been correlated. The cross correlation provides P waves with an accepted P duration. Typically, P waves that fail to correlate with the template are beats of ectopic origin and P waves with excessive noise.

Figure 10:
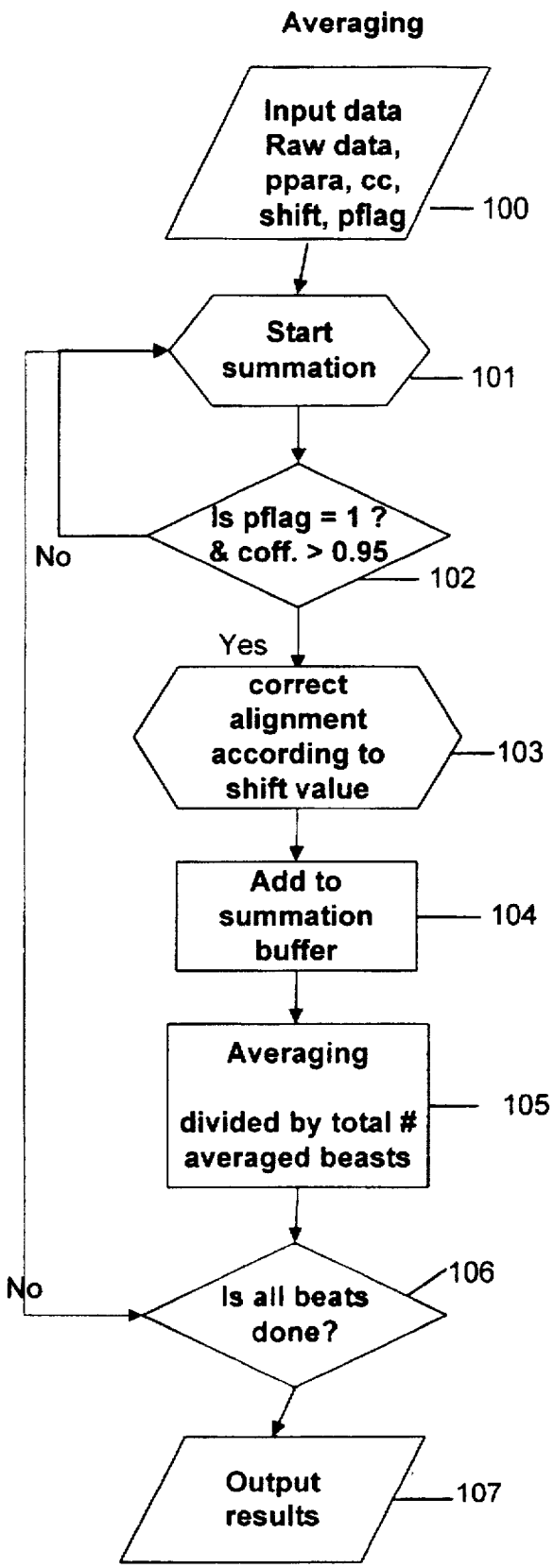
FIG. 10 is a flow diagram showing the P wave signal averaging portion of the method illustrated in FIG. 3.

The purpose of the subroutines 31–36 in FIG. 3 is to determine the alignment points of the P waves. With the alignment points determined, P wave averaging can be performed as shown in FIG. 10. The input to the averaging subroutine at 100 includes the raw X, Y and Z ECG lead data, the P wave parameters from step 67, the cross correlation coefficient from step 86, the shift necessary to align the P wave with the template from step 88 and the P flags from step 82. The summation begins at step 101. At step 102, the P wave is examined to see if the P flag equals one and the correlation coefficient is greater than 0.95. If not, the program returns to step 101 for the next P wave. If the P wave is qualified, that is, it is correctly aligned with the template according to the shift value at step 103, the program proceeds to step 104 where the signals are added in a summation buffer. The signals are then divided by the total number of averaged beats at step 105. If all the beats are completed at step 106, the output results are provided at 107. If not, the program returns to the start summation step 101 for the next beat.

The average P wave signals are delineated on the VM signal of the unfiltered P wave, as shown in FIG. 11 and the filtered P wave as shown in FIG. 12. For the unfiltered P wave delineation, the input parameters are the QRS delineation at 110. The onset and offset of the QRS signal are first determined at step 111. Then, the signal is low pass filtered using an eight sample point moving average of the P wave signal average at step 113 using the expression:

$$y_i = \frac{1}{8} \sum_{i=1}^{8} X_i$$

The vector magnitude is determined at step 114 from the expression:

$$VM = \sqrt{X^2 + Y^2 + Z^2}$$

The thresholds to detect unfiltered P onset and P offset points are based on baseline noise level. The mean and standard deviations of the base noise level are computed at step 115 and the thresholds are then set at step 116. In particular, threshold one (Th1) is the mean plus four standard deviations and threshold two (Th2) is equal to the mean plus six standard deviations. In order to estimate P onset, the system searches back forty milliseconds from the initial P onset at step 117 as shown in FIG. 11b. If four consecutive sample points are greater than Th1, the program proceeds to step 118, and if not, the program moves one sample point forward at step 117b and step 117a is repeated. At step 118, the program searches backward from Qon minus thirty milliseconds. At step 118a, the program determines if four consecutive sample points are greater than Th2 and if not, it moves one sample point backward at step 118b and step 118a is repeated.

FIG. 12a shows the filtered P-HIRES delineation. The input at 120 is the raw X, Y and Z high resolution signals. These are averaged at step 121 and then band pass filtered at step 122. Preferably, the user has the option of selecting several banned widths, such as, for example, 25–250 Hz, 40–250 Hz or 80–250 Hz.

The vector magnitude of the filtered signals is determined at step 123 using the expression:

$$VM = \sqrt{X^2 + Y^2 + Z^2}$$

This produces a filtered vector magnitude signal of the averaged P waves. At step 124, threshold one (Th1) for detecting P onset is set at mean plus three standard deviations of the noise level. Threshold two (Th2), for detecting P offset, is set at mean plus two standard deviations of the noise level. Then, at step 125, the initial P offset is set at the unfiltered P offset minus 20 milliseconds. At step 126a, the program determines if three consecutive sample points are smaller than Th2. If so, the program proceeds to step 127. If not, the program moves one sample point forward at step 126b and returns to step 126a for continuing to search. At step 127, the program determines if three consecutive sample points are smaller than Th1. If so, the program proceeds to step 128a. If not, the program moves one sample point backward at step 128b and returns to step 128a to continue the search. The output of the filtered P delineation at 129 includes filtered P onset and P offset which then can be used to calculate P duration, root mean-square voltage of the VM signal, and other P wave measurements. The filtered P-HIRES delineation provides high sensitivity and better separation between normal and patients with paroxysmal atrial fibrillation.

Figure 13B:
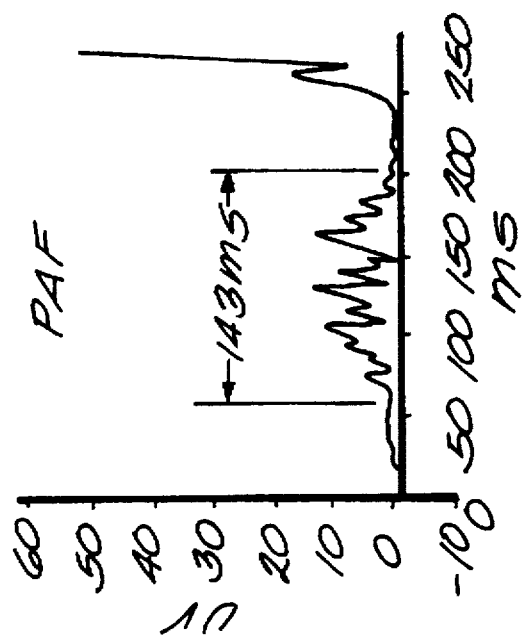
FIG. 13b shows a vector magnitude filtered P wave from a paroxysmal atrial fibrillation patient.
Figure 13A:
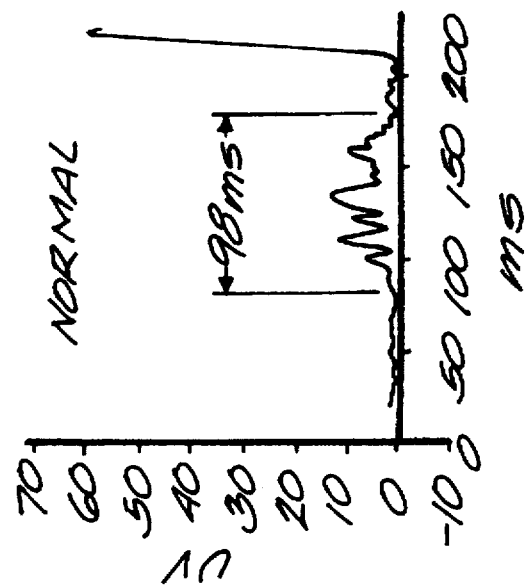
FIG. 13a shows a vector magnitude filtered P wave from a normal subject.

P-HIRES data was obtained on eighty subjects (forty-one males and thirty-nine females) with no cardiac history (normals) and fifty-one (twenty-seven males and twenty-four females) with PAF. The features that were examined include: P duration (filtered and unfiltered), RMS value of terminal forty milliseconds, thirty milliseconds and twenty millisecond portions, an integral of the whole P wave. It was found that the P wave duration was useful to differentiate normals from PAF patients. FIGS. 13a and 13b show two vector magnitude wave forms, with FIG. 13a being from a normal subject and FIG. 13b from a PAF patient. The P wave duration of the PAF patients is longer than that of the normal subjects. Results of studies shows that the P-HIRES analysis based on the method and apparatus according to the invention is useful to identify PAF patients. Among the time domain P wave parameters, it was found that only P duration is useful to differentiate PAF patients from normals. The parameter RMS value, which is useful in ventricular late potential detection is not as useful in P wave analysis. It is believed that one reason is that the signal to noise ratio in the P wave is so low that it is difficult to detect atrial late potentials from background noise.

While only a few embodiment of the invention has been illustrated and described, it is not intended to be limited thereby, but only by the scope of the appended claims.

We claim:

1. A method of averaging the P wave portion of ECG signals comprising the steps of, sensing human ECG signals having at least a QRS portion and a P wave portion, detecting the QRS portion of the ECG signals, suppressing the QRS portion of the ECG signals, generating a P wave detection function from the P wave portion of the ECG signals, cross correlating the detection functions of the P wave portions of the ECG signals, and averaging the cross correlated P wave detection function signals.

2. The method set forth in claim 1 and including the step of generating a P wave detection function template and cross the correlating the detection function of the P wave portions of the ECG signals with the template.

3. The method set forth in claim 2 wherein the template is generated by sampling a plurality of successive ECG wave forms, detecting the QRS portions of the ECG signals, suppressing the QRS portions of the ECG signals, generating a P detection function from the P wave portions of the ECG signals, selecting a seed beat from the P wave detection functions of the ECG signals, cross correlating the detection functions of the P wave portions of the ECG signals with the seed beat, averaging the cross correlated signals to provide the template.

4. The method set forth in claim 1 wherein the step of detecting the QRS portion of the ECG signals comprised defining the QRS portion and the step of suppressing the QRS portion of the ECG signals comprises subtracting the QRS portion of the signal from the ECG signal.

5. The method set forth in claim 1 wherein the ECG signals sensed include X, Y and Z ECG lead signals.

6. The method set forth in claim 1 wherein the step of generating the P detection function comprises filtering the ECG signal after suppression of the QRS portion, generating the vector magnitude of the P portions of X, Y and Z ECG lead signals, and low pass filtering the resultant signals.

7. The method set forth in claim 1 and including the steps of defining a P wave search zone, locating the signal peaks in the search zone, selecting the maximum peak, defining a P wave threshold and determining P wave on and P wave off markers within the search zone.

8. The method set forth in claim 1 wherein the step of cross correlating the P waves comprises the steps of computing the P-Q interval of the ECG signals, setting flags at the maximum and minimum levels of acceptable signals, and finding the maximum cross correlation co-efficient of the signals.

9. The method set forth in claim 1 wherein the ECG signals sensed include X, Y and Z lead signals, and including the step of generating a template of the P wave detection functions and cross correlating the detection functions of the P wave portions of the ECG signals with the template.

10. The method set forth in claim 9 and including the step of defining a P wave search zone, selecting the maximum peak in the search zone, and defining a P wave threshold in determining P wave on and off markers within the search zone.

11. The method set forth in claim 9 wherein the step of cross correlating the P waves comprises the steps of computing the P-Q interval of the ECG signals, setting flags at the maximum minimum levels of acceptable signals, and finding maximum cross correlation coefficient of the signals.

12. The method set forth in claim 11 wherein the step of generating the P detection function comprises filtering the ECG signals after suppression of the QRS portion, generating the vector magnitude of the P portion of the X, Y and Z ECG lead signals, and low pass filtering the resultant signals.

13. The method set forth in claim 12 wherein the step of detecting the QRS portion of the ECG signals comprises defining the QRS portion and the step of suppressing the QRS portion of ECG signals comprises subtracting the QRS portion of the signals from the ECG signals.

14. An apparatus for averaging the P wave portions of ECG signals and including, acquisition means for acquiring human ECG signals taken along the X, Y and Z axes and having at least a QRS portion and a P wave portion, means for detecting the QRS portions of the ECG signals, means for suppressing the QRS portion of the ECG signals, means for generating a P detection function of the ECG signals after suppression of the QRS portion, means for cross correlating the detection functions of the P wave portion of the ECG signals with a template and means for averaging the cross correlated detection functions of the P wave portions.

15. The apparatus set forth in claim 14 including means for defining a P wave search zone, means for locating the maximum signal peak in the search zone and means for defining a P wave threshold and for determining P wave on and P wave off markers within the search zone.

16. An apparatus for averaging the P wave portions of ECG signals and including, acquisition means for acquiring human ECG signals taken along the X, Y and Z axes and having at least a QRS portion and a P wave portion, processor means programmed for detecting the QRS portions of the ECG signals, for suppressing the QRS portions of the ECG signals, for generating a P detection function, for cross correlating the detection functions of the P waves with a template, and for averaging the cross correlated detection functions of the P waves.

17. A method of determining the filtered onset and offset of the P wave portion of ECG signals, comprising the steps of averaging at least a portion of the ECG signals, filtering the averaged signals, deriving the vector magnitude (VM) of the filtered averaged signals, determining the base noise level, and setting the P onset and P offset of the VM signals above the noise level.

18. The method set forth in claim 17 including the steps of setting a P offset threshold and a P onset threshold, setting the P offset by locating a first sample point of the vector magnitude signal at which a predetermined number of successive sample points from the first sample point are less than the initial P offset, and setting the P onset threshold by locating a second sample point of the vector magnitude signal which is a predetermined number of successive sample points forwardly from the second sample point are less than the P onset threshold.

19. The method set forth in claim 18 and including the step of low pass filtering the ECG signal portion prior to determining the vector magnitude of said signals.

20. The method set forth in claim 19 wherein said ECG signals are taken along the X, Y and Z axes.

21. The method set forth in claim 18 and including the step of band pass filtering the ECG signals prior to determining the vector magnitude of said signals.

22. The method set forth in claim 21 wherein said ECG signals are taken along the X, Y and Z axes.

23. An apparatus for determining the onset and offset of the P wave portion of ECG signals, including means for averaging at least a portion of the ECG signals, means for filtering the average signals, means for deriving the vector magnitude of the filter average signals, means for determining the base noise level, and means for setting the P onset and P offset of the vector magnitude signals above the noise level.

24. An apparatus for averaging the P wave portions of ECG signals and including, acquisition means for acquiring human ECG signals, processor means programmed to detect the QRS portions of the ECG signals, to suppress the QRS portions of the ECG signals, to generate a P detection function, to derive a template of the P wave detection functions, to cross correlate the P wave with the template, and to average the cross correlated P waves.

25. The apparatus set forth in claim 24 wherein said processor is further programmed to generate a P wave detection function template and to cross the correlating the detection function of the P wave portions of the ECG signals with the template.

26. The apparatus set forth in claim 24 wherein said processor is further programmed to detect the QRS portion of the ECG signals by defining the QRS portion and to suppress the QRS portion of the ECG signals by subtracting the QRS portion of the signal from the ECG signal.

27. The apparatus set forth in claim 24 wherein said processor is further programmed to generate the P detection function by filtering the ECG signal after suppression of the QRS portion, to generate the vector magnitude of the P wave detection functions portions of X, Y and Z ECG lead signals, and to low pass filter the resultant signals.

28. The apparatus set forth in claim 24 wherein said processor is further programmed to define a P wave search zone, to locate the signal peaks in the search zone, to select the maximum peak, to define a P wave threshold and to determine P wave on and P wave off markers within the search zone.

29. The apparatus set forth in claim 24 wherein said processor is further programmed to cross correlate the P waves by computing the P-Q interval of the ECG signals, to set flags at the maximum and minimum levels of acceptable signals, and to find the maximum cross correlation co-efficient of the signals.

* * * * *